United States Patent
Kadrmas

(10) Patent No.: US 7,659,260 B2
(45) Date of Patent: Feb. 9, 2010

(54) TAMPONADE COMPOSITIONS AND METHODS FOR RETINAL REPAIR

(76) Inventor: Eddie Francis Kadrmas, 34 Windermere Ct., Plymouth, MA (US) 02360

( * ) Notice: Subject to any disclaimer, the term of this patent is extended or adjusted under 35 U.S.C. 154(b) by 200 days.

(21) Appl. No.: 11/035,748

(22) Filed: Jan. 14, 2005

(65) Prior Publication Data

US 2006/0159771 A1 Jul. 20, 2006

(51) Int. Cl.
*A61K 31/70* (2006.01)
(52) U.S. Cl. .......................... 514/62; 514/915
(58) Field of Classification Search ................... 514/62, 514/915
See application file for complete search history.

(56) References Cited

U.S. PATENT DOCUMENTS 5,627,162 A * 5/1997 Gwon et al. ................... 514/54
6,492,503 B1 12/2002 Kariya et al.

OTHER PUBLICATIONS

Kobuch et al., "New substances for intraocular tamponades: perfluorocarbon liquids, hydrofluorocarbon liquids and hydrofluorocarbon-oligomers in vitreoretinal surgery," *Graefe's Arch Clin Exp Ophthalmol* vol. 239, pp. 635-642 (2001).

Sandner and Engelmann, "First experiences with high-density silicone oil (densiron) as an intraocular tamponade in complex retinal detachment," *Graefe's Arch Clin Exp Ophthalmol* www.springerlink.com (2005).

Yamamoto and Takeuchi, "Silicone oil and fluorosilicone," *Seminars in Ophthalmology* vol. 15, No. 1, pp. 15-24 (2000).

Eckardt et al., "Experimental intraocular tolerance to liquid perfluorooctane and perfluoropolyether," Retina. 11(4):375-84 (1991). (Abstract Only).

Orzalesi et al., "Experimental short-term tolerance to perfluorodecalin in the rabbit eye: a histopathological study," Curr. Eye Res. 17(8):828-35 (1998). (Abstract Only).

Velikay et al., "The effect of chemical stability and purification of perfluorocarbon liquids in experimental extended-term vitreous substitution," Graefes Arch. Clin. Exp. Ophthalmol. 233(1):26-30 (1995). (Abstract Only).

Perfluoron Package Insert, Alcon, Fort Worth, TX, 2001.

\* cited by examiner

*Primary Examiner*—Zohreh A Fay
(74) *Attorney, Agent, or Firm*—Fish & Richardson P.C.

(57) ABSTRACT

Described herein are methods of repairing retinal tissue using resorbable tamponade compositions that are heavier than aqueous humor and contain one or more glysosaminoglycans.

8 Claims, No Drawings

TAMPONADE COMPOSITIONS AND METHODS FOR RETINAL REPAIR

TECHNICAL FIELD

Described herein are tamponade compositions and methods for retinal repair.

BACKGROUND

The retina is a thin tissue that lines the inner wall of the eye. It contains photoreceptors that convert light that enters the eye into nervous impulses that transmit visual information to the brain. The macula is a small portion of the retina that contains a high density of photoreceptors and, thus, provides the ability to see fine detail. Trauma, disease, infection, and the process of aging can result in insults to the retina, such as holes, tears, and retinal detachments from the inner wall of the eye. If left untreated, these insults can lead to severely impaired vision.

Procedures for repairing the retina include procedures for sealing retinal tears and holes with laser surgery and cryopexy (use of a freezing probe). These procedures scar retinal tissue, thereby sealing breaks in the tissue. However, any unsealed breaks can enlarge and/or lead to fluid seepage underneath the retina, i.e., between the retina and the inner wall of the eye. Seepage of fluid into this space can prevent tissue repair and lead to retinal detachment.

SUMMARY

The new therapeutic methods and compositions described herein are based, at least in part, on the discovery that certain compositions, which are denser than aqueous humor and include one or more glycosaminoglycans (GAGs), are useful as "tamponade compositions" for the repair of retinal insults such as retinal detachments (e.g., inferior retinal detachments) and macular holes. New methods are described that include administering a tamponade composition into the vitreous cavity of an eye in a procedure for repairing a retinal insult, for example, an inferior retinal detachment or a macular hole. New tamponade compositions are disclosed that include (i) a non-toxic liquid that is denser than aqueous humor, e.g., deuterium-containing heavy water, and (ii) one or more GAGs.

The new therapeutic methods and compositions disclosed herein have a number of advantages. Tamponade compositions are denser than aqueous humor. Therefore, they can be used in procedures to repair inferior retinal tears and macular holes, without requiring awkward post-operative positioning of a subject's head. The new compositions are effective as tamponades due to their high interfacial tension, high surface tension, and high viscosity. Their high surface tension and high interfacial tension provides the new compositions with the ability to press the retinal tissue against the inner wall of the eye, thereby keeping the tissue in place and preventing later detachment. The high surface tension and high interfacial tension of the new compositions also prevent the new composition (and other liquids in the eye) from seeping through any tissue breaks (e.g., breaks that remain or develop after cryopexy or laser surgery) and into the space between the retina and the inner wall of the eye. This seepage prevention allows the retina to heal and reattach. The high viscosity of the new compositions prevents them from readily mixing with the aqueous humor in the eye, thus largely maintaining the integrity of the tamponade composition, even when contacted with aqueous humor.

In one aspect, described herein are tamponade composition that include (i) a non-toxic, resorbable liquid that is denser than aqueous humor and (ii) one or more glycosaminoglycans (GAGs). In certain embodiments, a tamponade composition includes one or more of the following non-toxic liquids that are denser than aqueous humor: deuterium-containing heavy water ($D_2O$) or an aqueous solution of sucrose, glycerol, dextran or the like. In some examples, a tamponade composition includes at least about 5% or at least about 10% $D_2O$ by volume. In other examples, a tamponade composition includes from about 10% to about 25% $D_2O$ by volume. In still other examples, a tamponade composition includes from about 25% to about 50% D2O by volume. In yet other examples, a tamponade composition includes about 50% or more $D_2O$ by volume.

In some embodiments, a tamponade composition includes one or more of the following GAGs: hyaluronic acid, chondroitin sulfate, keratan sulfate, keratan sulfate II, heparan sulfate, and dermatan sulfate. Certain tamponade compositions include concentrations of at least about 0.01 mg GAG per ml, at least about 0.05 mg GAG per ml, at least about 0.1 mg GAG per ml, or at least about 0.9 mg GAG per ml. Some tamponade compositions include a concentration of GAG that is from about 0.05 to about 0.9 mg GAG per ml, or from about 0.9 mg to about 2 mg GAG per ml, or from about 2 mg to about 5 mg GAG per ml, or from about 5 mg to about 10 mg GAG per ml, or from about 10 mg to 20 mg GAG per ml. In one example, a tamponade composition includes (i) deuterium-containing heavy water and (ii) from about 0.05 mg to about 0.9 mg of hyaluronic acid per ml of composition. In another example, a tamponade composition includes (i) deuterium-containing heavy water and (ii) from about 0.9 mg to about 10 mg of hyaluronic acid per ml of composition. In still another example, a tamponade composition includes (i) deuterium-containing heavy water, (ii) from about 0.05 mg to 0.9 mg hyaluronic acid per ml of composition, and (iii) about 0.01 mg or more of chondroitin sulfate per ml of composition. In yet another example, a tamponade composition includes (i) deuterium-containing heavy water, (ii) from about 0.05 mg to about 5 mg hyaluronic acid per ml of composition, and (iii) about 0.01 mg or more of chondroitin sulfate per ml of composition.

The tamponade compositions described above can be used in the preparation of a medicament (e.g., an intraocular medicament) for use in treating a retinal break (e.g., an inferior retinal detachment or macular hole). The medicament is suitable for use in a method that involves the intraocular injection into the vitreous cavity of an eye following vitrectomy.

In another aspect, described herein is a method of treating a break in retinal tissue in a subject. The method includes (i) removing the vitreous humor from the vitreous cavity of the subject's eye and (ii) administering into the vitreous cavity an amount of a tamponade composition sufficient to cover the retinal detachment or the macular hole. The tamponade composition used in this method (a) is denser than aqueous humor and (b) comprises a glycosaminoglycan and a non-toxic, resorbable liquid. In some embodiments, the tamponade compositions used in the method include a concentration of at least about 0.01 mg GAG per ml, at least about 0.05 mg GAG per ml, at least about 0.1 mg GAG per ml, or at least about 0.9 mg GAG per ml. In some embodiments, the tamponade compositions used in the method include a concentration of GAG (for example, hyaluronic acid) that is from about 0.05 mg to about 0.9 mg GAG per ml, or from about 0.9 mg to about 2 mg GAG per ml, or from about 2 mg to about 5 mg GAG per ml, or from about 5 mg to about 10 mg GAG per ml, or from about 10 mg to 20 mg GAG per ml. Optionally, the method includes administering a tamponade composition that includes about 0.01 mg, or more, of chondroitin sulfate in addition to a GAG (for example, hyaluronic acid. In some embodiments, the tamponade composition used in the method includes at least 5% D2O by volume. In some examples, the tamponade composition used in the method includes from about 10% to about 25% D2O by volume, or from about 25% to about 50% D2O by volume, or about 50% or more D2O by volume.

In some embodiments, the method includes administering enough tamponade composition to obtain an initial fill of at least 10% of the volume of the vitreous cavity of the eye. In some examples, the method includes administering enough tamponade composition to an initial fill of from about 10% to about 25% of the volume of the vitreous cavity. In other examples, the method includes administering enough tamponade composition to an initial fill of from about 25% to about 50% of the volume of the vitreous cavity. In still other examples, the method includes administering enough tamponade composition to an initial fill of about 50% or more of the volume of the vitreous cavity.

In some embodiments, the method further includes administering a tamponade agent, such as a gas or silicone-based oil to treat (i) concomitant superior and an inferior retinal detachments or (ii) concomitant superior retinal detachment and macular hole.

In some embodiments, the method further includes selecting a patient that has an inferior retinal detachment or a macular hole.

As used herein, "a non-toxic liquid" is a liquid that is not toxic when administered into the vitreous cavity of the eye of a subject in an amount that is less than or equal to the volume of the vitreous cavity.

As used herein, a "tamponade composition" is a composition that is denser than aqueous humor, and that includes one or more GAG.

As used herein, "tamponade agents" include gases and silicone oils that are used as tamponades in art-known retinal repair procedures.

"Silicone oil", as used herein, refers to silicone oils and silicone copolymer oils.

A "subject," as used herein, refers to a human or a non-human animal, e.g., a dog, cat, pig, sheep, goat, monkey, fish, bird, etc.

The details of one or more embodiments of the invention are set forth in the accompanying drawings and the description below. Other features, objects, and advantages of the invention will be apparent from the description and drawings, and from the claims.

DETAILED DESCRIPTION

Described herein are new methods and compositions for repairing retinal insults, such as, inferior retinal detachments and macular holes. Generally, the new methods include the use of tamponade compositions instead of a gas or a silicone oil in modified versions of procedures such as pneumatic retinopexy and variations of pneumatic retinopexy that include vitrectomy.

Diagnosing Retinal Insults

Symptoms of retinal detachment include the appearance of light flashes, wavy or watery vision, a veil- or curtain-like visual obstruction, a large number of floaters, or a sudden loss of vision. Symptoms of a macular hole include blurred central vision, distorted vision, difficulty reading or seeing detail, gray area in central vision, or a central blind spot. Clinicians use ophthalmoscopy or ultrasound imaging to identify the type and anatomical location of a retinal insult. For example, ophthalmoscopy or ultrasound imaging can identify and distinguish between inferior retinal tears or detachments, superior retinal tears or detachments, and/or macular holes in a subject.

Known Methods for Repairing Retinal Insults

Retinal detachments can be treated by scleral buckle surgery, pneumatic retinopexy, or variations of these procedures.

In scleral buckle surgery, a sponge or silicone band deforms the eye wall, pressing it inwards towards the center of the eye. This buckling of the eye relieves traction on the detached retinal tissue and brings the detached tissue into contact with the (buckled) interior wall of the eye.

Pneumatic retinopexy (PR) involves the injection of a gas bubble into the vitreous cavity. The bubble presses the detached portion of the retina towards the interior wall of the eye, thereby joining the detached portion of the retina to undetached portion. Since gases rise in solution, PR is more effective for the treatment of upper (superior) retinal detachments.

Both scleral buckle surgery and PR are typically followed by laser surgery or cryopexy to seal breaks in the tissue and to hold the formerly-detached tissue in place while it reattaches to the inner wall of the eye.

Variations of PR include the extraction of vitreous humor from the vitreous chamber of the eye (vitrectomy) prior to the injection of (i) a gas bubble or (ii) silicone oil. In one variation, a vitrectomy is followed by the insertion of a viscous liquid, such as perfluoron into the vitreous chamber. The perfluoron pushes detached retinal tissue back into contact with the inner wall of the eye. The retinal tissue is then cauterized in place, e.g., by laser surgery. The perfluoron is then extracted, and the vitreous chamber is filled with a tamponade agent. Known tamponade agents include gases, such as perfluoropropane ($C_3F_8$) or sulfur hexafluoride ($SF_6$), or liquids, such as silicone oils and silicone copolymer oils. These gases and silicone oils represent art-known tamponade agents that press against the reattached tissue, thereby helping to hold it in place.

Since gas tends to rise in solution, gaseous tamponade agents are most effective for the repair of retinal detachments from the superior portion of the eye. Following injection of the gas bubble into the vitreous chamber, aqueous humor is secreted into the vitreous chamber as the gas bubble is resorbed. Thus, a gaseous tamponade agent becomes a shrinking bubble trapped above a growing pool of aqueous humor. When a subject's head is held in a normal upright position, the gas bubble presses against the superior portion of the retina, while the aqueous humor presses against the inferior portion of the retina. Use of a gas tamponade to treat an inferior retinal detachment generally requires positioning and post-operatively maintaining the subject's head in an abnormal position. For example, the subject could be required to hang upside-down or to lie face downward to ensure that the gas bubble maintains contact with the inferior portion of the retina.

Silicone or silicone copolymer oils can be used more readily than gas bubbles as tamponade agents in the repair of inferior retinal detachments. However, these oils appear to be associated with long term complications, such as cataracts, glaucoma, and keratopathy. Since these oils are not resorbed, a second surgical procedure is needed to remove the oil. Removal of the oil itself has been reported to lead to other complications such as retinal redetachment due to reproliferation of epiretinal membranes and increasing traction on the retina.

New Methods for Repairing Retinal Insults

A method of repairing a retina includes the use of a tamponade composition that is denser than aqueous humor and that includes one or more glycosaminoglycans (GAGs). The density of aqueous humor is nearly identical to water (1000 kg/m$^{-3}$) at 37° C. GAGs are unbranched (linear) polysaccharides that consist of repeating units of a disaccharide. GAG disaccharides can include amino sugars, e.g., N-acetylgalactosamine (GlcNAc) or N-acetylglucosamine (GalNAc), uronic acids e.g., glucuronate (GlcA) or iduronate (IdoA)), and/or other sugars, e.g., galactose (Gal). GAGs are highly negatively charged molecules, with extended conformation that imparts high viscosity to the solution. Naturally occurring GAGs can be found on the surface of cells or in the extracellular matrix (ECM).

The tamponade compositions can be introduced into the eye instead of a gas or silicone-based oil in pneumatic retinopexy procedures and variations thereof.

The new methods of repairing a retina can be used in conjunction with pneumatic retinopexy or a variation thereof to treat subjects suffering from concomitant retinal detachments in both the superior and inferior portion of the eye. For example, following removal of perfluoron in a variation of pneumatic retinopexy, both a gas (e.g., $C_3F_8$ or $SF_6$) and a tamponade composition described herein are introduced into the vitreous chamber of the eye. In this procedure, both the inferior and superior detachments are treated at the same time.

The tamponade compositions can also be used as a general intraoperative tool to aid flattening the retina.

Generally, in the new methods for repairing an inferior retina, the post-operative subject should maintain a sitting to supine, semirecumbent position during sleep. At other times, the post-operative subject should remain upright. The positioning is important for keeping the tamponade composition (and the tamponade gas in methods for treating concomitant inferior and superior detachments) in contact with the retinal tissue being treated.

If it should become desirable to reduce or eliminate the glycosaminoglycans (GAGs) introduced to the eye by a tamponade composition, a pharmaceutical composition comprising an enzyme that degrades a GAG can be introduced into the eye. Reduction or elimination of GAGs can be desirable if, for example, GAGs from the tamponade are insufficiently resorbed, or if complications develop that are associated with GAGs in the tamponade. Enzymes that degrade GAGs are known in the art. For example, hyaluronic acid can be degraded by any one of multiple known types of hyaluronidases, β-glucuronidase, and/or β-N-acetylhexosaminidase. In another example, chondroitin sulfate can be degraded using GalNAc-6-SO$_4$ sulfatase, GalNAc-4-SO$_4$ sulfatase, β-N-acetylhexosaminidase (A or B) and/or β-glucuronidase. In still other examples, bacterial keratanases as well as animal exoglycosidases (β-galactosidase and β-hexosaminidase) can be used to degrade keratan sulfate. Combinations of sulfatases and endoglucuronidase can be used to degrade heparin sulfate.

Tamponade Compositions

A tamponade composition can include any non-toxic liquid that, when mixed with a GAG, results in a solution that is denser than aqueous humor. In certain embodiments, the non-toxic liquid is deuterium-containing heavy water ($D_2O$). Heavy water has a relative density of 1.1044 at 25° C., and it has a relative density of between 1.1001 and 1.019 at 35-40° C. (*Handbook of Chemistry and Physics*, 73$^{rd}$ Ed, Ch 6, pg. 13 (CRC Press, Boca Raton, Fla. 1992). Deuterium-containing heavy water is reportedly non-toxic, unless ingested in very large amounts. In some embodiments, the non-toxic liquid can be an aqueous solution that is denser than aqueous humor, e.g., an aqueous solution of sucrose, glycerol, or dextran. In other embodiments the non-toxic liquid can be a physiological buffer that is denser than water. In some embodiments, the non-toxic liquid can be water, providing that it is mixed with enough GAG so that the resulting tamponade composition is denser than aqueous humor.

Exemplary GAGs for use in a tamponade composition include hyaluronic acid (HA), chondroitin sulfate (CS), keratan sulfate (KS), keratan sulfate II (KSII), dermatan sulfate (DS), and heparan sulfate (HS). HA includes repeating units of GalNAc β(1, 3) GlcA β(1, 4) disaccharides (in keeping with convention, each sugar residue is followed by a description of the linkage type between that residue and the following sugar residue). CS is composed of repeating units of GalNAc β(1, 4) GlcA β(1, 3) disaccharide. KS and KS II are composed of repeating units of a Gal β(1, 4) GlcNAc β(1, 3) disaccharide, the difference being that KS is linked to proteins via N-linkage and KS II is linked to proteins via O-linkage. DS can refer to any glycan that contains one or more iduronate disaccharides, e.g., GalNAc β(1, 4) IdoA β(1, 3) disaccharide (also known as chondroitin sulphate B). HS is composed of repeating units of GlcNAc α(1,4) GlcA β(1, 4) disaccharide. Although they are similar in carbohydrate structure, HS can be distinguished from heparin, which generally should not be used as the GAG in a tamponade composition. HS undergoes less extensive (i) sulfation and (ii) uronic acid epimerization relative to heparin. HS is also manufactured nearly ubiquitously in vivo, whereas heparin is almost exclusively manufactured by mast cells and heparin has much higher anticoagulant activity.

GAG salts are available commercially from vendors such as Sigma (St. Louis, Mo.) and Associates of Cape Cod, Inc. (ACC) (Falmouth, Mass.). GAGs can also be purified from animal or plant tissues. Some GAGs can be synthesized. For example, KS or KS II can be manufactured using molecular biology and biochemical techniques, e.g., as described in Akama et al., *J. Biol. Chem.*, 277:42505-42513, 2002.

Commercial mixtures of GAGs are also available. For example VISCOAT™ (Alcon USA, Ft. Worth, Tex.) is a physiological buffer that contains up to 40 mg sodium chondroitin sulphate and 30 mg sodium hyaluronic acid per ml.

New tamponade compositions disclosed herein generally include (i) a liquid that is denser than aqueous humor and (ii) a GAG. Preferred tamponade compositions include a liquid that is more viscous than water. Liquids that are denser than aqueous humor and more viscous than water include heavy water and aqueous solutions of sucrose, glycerol, or dextran. New tamponade compositions can include any GAG. Preferred tamponade compositions include hyaluronic acid (HA) or a combination of HA and chondroitin sulfate(CS).

The following describe exemplary new tamponade compositions: (i) a solution that includes at least 2 mg/ml HA in a liquid that contains at least 25% deuterium-containing heavy water (heavy water), (ii) a solution that includes 1.5-2 mg/ml HA in a liquid that contains at least 25% heavy water, (iii) a solution of between 1.25-1.5 mg/ml HA in a liquid that contains at least 25% heavy water (iv) a solution of between 1.0-1.24 mg/ml HA a liquid that contains at least 25% heavy water, (v) a solution of between 0.75-0.99 mg/ml HA in a liquid that contains at least 25% heavy water (vi) a solution of between 0.5-0.74 mg/ml HA in a liquid that contains at least 25% heavy water (vii) a solution of between 0.25-0.49 mg/ml HA in a liquid that contains at least 25% heavy water (viii) a solution of between 0.1-0.24 mg/ml HA in a liquid that contains at least 25% heavy water (ix) a solution of no more than 0.1 mg/ml HA in a liquid that contains at least 25% heavy water.

Pharmaceutical Compositions

The tamponade compositions described herein can be prepared as pharmaceutical compositions suitable for delivery into the eye. Preparation as a pharmaceutical composition can involve no more than ensuring that the tamponade composition is sterile enough for intraocular administration. A pharmaceutical composition can also include solvents, GAG stabilizing agents, antibacterial and antifungal agents, and the like, that are compatible with pharmaceutical administration.

Sterile pharmaceutical compositions can be manufactured by preparing a tamponade composition described herein and then filter-sterilizing the tamponade composition. In other methods of manufacturing a pharmaceutical composition, a non-toxic liquid for a tamponade composition, and a GAG are sterilized separately, and then combined under sterile conditions to form a sterile pharmaceutical composition comprising a tamponade composition.

A pharmaceutical composition comprising a tamponade composition can also be manufactured by preparing a powder of a GAG. A sufficient quantity of sterile, e.g., filter sterilized, non-toxic liquid for a tamponade composition can be combined with the GAG powder to solubilize the GAG and thereby form a pharmaceutical composition of a tamponade composition. GAG powder can be prepared by vacuum-drying or freeze-drying a GAG solution.

EXAMPLES

The invention is further described in the following examples, which do not limit the scope of the invention described in the claims.

Example 1

The following is an exemplary protocol for a new procedure of repairing an inferior retinal detachment. A patient is diagnosed with an inferior retinal tear. However, the procedure is contraindicated in patients that are aphakic or in patients that have an anterior-chamber intraocular implant without an intact posterior capsule.

A standard 3-port vitrectomy is performed on the patient's eye, followed by a core vitrectomy. The vitreous base is shaved with the aid of scleral depression for 360 degrees. The break is isolated and freed from any traction. If there are any pre- or subretinal membranes, they should be removed/segmented. The retina is then reattached either by (a) introducing perfluorocarbon (e.g., perfluoroctane) liquid or (b) subretinal drainage via a retinotomy or existing break during an air-fluid exchange. A laser is then used to photocoagulate or seal the break. Additional laser is applied 360 degrees to the far peripheral retina in circlage. If used, the perfluorocarbon liquid is removed as part of an air-fluid exchange.

At this point in the procedure, a tamponade composition including from 0.1 mg to 3 mg hyaluronic acid (HA)/ml is injected under a complete air fill in the case of an inferiorly located detachment/break. The tamponade composition preferably fills at least ½–⅔ of the eye volume, the remainder of the vitreous cavity is filled with air.

In the post-operative period, the patient is instructed to sleep in the sitting-up to supine, semirecumbant position. Generally, the tamponade composition is allowed to resorb. Optionally, to degrade the HA introduced into the eye by a tamponade composition, a hyaluronidase containing pharmaceutical composition such as VITRASE™ (ISTA Pharmaceutical, Irvine, Calif.) is added.

Example 2

The following is an exemplary protocol for a new procedure of repairing a macular hole. A patient is diagnosed with a macular hole that cannot be surgically repaired using standard techniques with intraocular gas because the patient cannot remain prone.

A standard vitrectomy is performed as in Example 1. A membrane peel over the macula is performed, followed by an air-fluid exchange. A tamponade composition is injected under air to fill at least ⅔ to ¾ of the eye volume. In the post-operative period, the patient is instructed to remain upright during the day, but may assume the supine position during sleep.

Example 3

To test the ability of tamponade compositions to repair detached retinas, isolated pig eyes were used as standard surgical models. Pig eyes were obtained by overnight shipment from a slaughter house. A lensectomy was performed to remove the lenses, which typically become opaque in non-living eyes and inhibit the view of the retina. Retinal detachments were created with different sizes and numbers (i.e., single or multiple) of breaks in different pig eyes. Each retina was flattened via the drainage of subretinal fluid through the break during an air-fluid exchange. Tamponade compositions were then injected into the eyes with the aid of a viscous fluid injector using a 27 gauge cannula. Eyes were filled to 50% capacity. The tamponade compositions used varied in concentrations of GAG. In some experiments, HA solution was mixed with heavy water (SIGMA) to obtain solutions containing between 0.5 to 0.67 mg HA per ml. In some experiments the tamponade compositions were made by mixing solution of VISCOAT™ (Alcon USA Inc., Ft. Worth, Tex.) with heavy water to form solutions containing from 1.5 to 2 mg HA per ml and 2 to 2.67 mg chondroitin sulfate (CS) per ml.

All eyes with retinal detachments tested were seen to reattach and stay attached for up to 24 hours after the procedure. Additionally, eyes that were purposely left partly detached following drainage of subretinal fluid were seen to reattach due to the effect of the tamponade liquid on the vitreoretinal interface. The tamponade composition comprising both HA and CS demonstrated greater tamponade effect than the tamponade composition comprising HA alone.

These results indicate that tamponade compositions are suitable for use (i) as an intraoperative tool for flattening the retina and (ii) in the repair inferior retinal detachments.

Example 4

Rabbits (New Zealand White) were anesthetized with pentobarbital and one eye was subjected to the vitrectomy technique described in Example 1. Each eye was filled to 50% capacity with tamponade compositions described in Example 3. Each eye was then closed using standard techniques. Eyes were monitored post-operatively for inflammation and lens clarity.

At two weeks, no marked inflammation or elevation of intraocular pressure was observed. The lenses appeared relatively clear. Approximately 50% of the original volume of the tamponade composition remained. These results indicate that the tamponade compositions used were non-toxic and resorbable.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a break in retinal tissue in a subject, the method comprising:
   removing the vitreous humor from the vitreous cavity of the subject's eye; and
   administering into the vitreous cavity an amount of a tamponade composition sufficient to cover the retinal detachment or the macular hole, wherein the tamponade composition comprising:
   (a) a non-toxic, resorbable liquid that is denser than aqueous humor, wherein said liquid is deuterium-containing heavy water, and
   (b) at least one glycosaminoglycan selected from the group consisting of hyaluronic acid, chondroitin sulfate, keratan sulfate, keratan sulfate II, heparan sulfate, and dermatan sulfate and a non-toxic, resorbable liquid that is denser than aqueous humor.

2. The method of claim 1, wherein the tamponade composition comprises about 0.05 mg of the glycosaminoglycan per milliliter of the composition.

3. The method of claim 2, wherein the glycosaminoglycan is hyaluronic acid.

4. The method of claim 3, wherein the tamponade composition further comprises about 0.05 mg of chondroitin sulfate per milliliter of the composition.

5. The method of claim 1, wherein the tamponade composition comprises from about 0.9 mg to 5 mg of the glycosaminoglycan per milliliter of the composition.

6. The method of claim 5, wherein the glycosaminoglycan is hyaluronic acid.

7. The method of claim 6, wherein the tamponade composition further comprises about 0.05 mg of chondroitin sulfate per milliliter of the composition.

8. The method of claim 1, wherein the subject has (i) a superior retinal detachment and (ii) an inferior retinal detachment or a macular hole, and the method further comprises administering a gaseous tamponade agent to the vitreous cavity of the eye.

* * * * *